(12) United States Patent
Alt

(10) Patent No.: US 6,387,121 B1
(45) Date of Patent: May 14, 2002

(54) VASCULAR AND ENDOLUMINAL STENTS WITH IMPROVED COATINGS

(75) Inventor: Eckhard Alt, Ottobrunn (DE)

(73) Assignee: Inflow Dynamics Inc., Wilmington, DE (US)

( * ) Notice: Subject to any disclaimer, the term of this patent is extended or adjusted under 35 U.S.C. 154(b) by 0 days.

(21) Appl. No.: 09/634,667

(22) Filed: Aug. 8, 2000

Related U.S. Application Data

(63) Continuation-in-part of application No. 09/175,919, filed on Oct. 20, 1998, now Pat. No. 6,099,561, which is a continuation-in-part of application No. 09/059,053, filed on Apr. 11, 1998, now abandoned, which is a continuation-in-part of application No. 08/733,553, filed on Oct. 21, 1996, now Pat. No. 5,824,045.

(51) Int. Cl.$^7$ .................................................. A61F 2/06
(52) U.S. Cl. .................................................... 623/1.15
(58) Field of Search ................................ 623/1.1, 1.11, 623/1.12, 1.13, 1.14, 1.15, 1.16, 1.17, 1.18, 1.19, 1.2, 1.21, 1.22, 1.44, 1.45, 1.46; 606/191, 194, 198

(56) References Cited

U.S. PATENT DOCUMENTS

| | | | | | |
|---|---|---|---|---|---|
| 5,628,787 A | * | 5/1997 | Mayer | ............................. | 623/1 |
| 5,649,951 A | * | 7/1997 | Davidson | ..................... | 606/198 |
| 5,649,977 A | * | 7/1997 | Campbell | ........................ | 623/1 |

* cited by examiner

*Primary Examiner*—Michael J. Milano
*Assistant Examiner*—Vy Q. Bui

(57) ABSTRACT

A stent has a tubular metal base adapted to be expanded from a first vessel-navigable diameter to a larger second vessel-deployed diameter; a thin, continuous intermediate layer of noble metal or alloy thereof selected from a group consisting of niobium, zirconium, titanium and tantalum, overlying and tightly adherent to an exposed surface area of the tubular metal base; and a biocompatible outer layer of iridium oxide overlying and adherent to the intermediate layer. The outer layer has a relatively rough surface with interstices into which beneficial drugs or other substances or agents may be infused, with or without a biodegradable carrier, to preclude occlusion from restenosis or thrombosis during the acute stage following deployment of the stent.

10 Claims, 1 Drawing Sheet

VASCULAR AND ENDOLUMINAL STENTS WITH IMPROVED COATINGS

CROSS-REFERENCE TO RELATED APPLICATIONS

This application is a continuation-in-part of patent application Ser. No. 09/175,919, filed Oct. 20, 1998 now U.S. Pat. No. 6,099,561, issued Aug. 8, 2000 ("the '561 patent"), which is a continuation-in-part of Ser. No. 08/733,553 filed on Oct. 21, 1996 U.S. Pat. No. 5,824,045, issued Oct. 20, 1998 ("the '045 patent"), and of application Ser. No. 09/059,053, filed Apr. 11, 1998 now abandoned ("the '053 application"), each of which has the same inventor and assignee as the instant application.

BACKGROUND OF THE INVENTION

The present invention relates generally to stents which are implantable or deployable in a vessel or duct within the body of a patient to maintain the lumen of the duct or vessel open, and more particularly to improvements in stent coatings and in methods for applying such coatings.

When inserted and deployed in a vessel, duct or tract of the body, for example a coronary artery after dilatation of the artery by balloon angioplasty, a stent acts as a prosthesis to maintain the vessel, duct or tract (generally referred to as a vessel for convenience herein) open. The stent has the form of an open-ended tubular element with openings through its sidewall to enable its expansion from a first outside diameter which is sufficiently small to allow the stent to traverse the vessel to reach a site where it is to be deployed, to a second outside diameter sufficiently large to engage the inner lining of the vessel for retention at the site.

An occluded coronary artery, for example, is typically attributable to a buildup of fatty deposits or plaque on the inner lining of the vessel. A balloon angioplasty procedure is the treatment of choice to compress the deposits against the inner lining of the vessel to open the lumen. Alternatively, removal of plaque may be achieved. by laser angioplasty, or by rotationally cutting the material into finely divided particles which are dispersed in the blood stream. The problem with angioplasty for a large segment of cardiac patients is that a new blockage appears within only weeks after the angioplasty procedure, attributable to trauma to the blood vessel wall from the angioplasty. The mechanism responsible for the new blockage is intimal hyperplasia, i.e., a rapid proliferation of smooth muscle cells in the affected region of the wall. Thus, many patients suffer restenosis, or re-occlusion of the vessel lumen.

The customary procedure is to install a stent at the trauma site at the time of or shortly after the angioplasty is performed. The stent is deployed by radial expansion under outwardly directed radial pressure exerted, for example, by active inflation of a balloon of a balloon catheter on which the stent is mounted. In some instances, passive spring characteristics of a pre-formed elastic stent serves the purpose. The stent is thus expanded to engage the inner lining or inwardly facing surface of the vessel wall with sufficient resilience to allow some contraction but also with sufficient stiffness to largely resist the natural recoil of the vessel wall.

The presence of the stent in the vessel, however, tends to promote thrombus formation as blood flows through the vessel, which results in an acute blockage. The thrombosis and clotting can be reduced or even eliminated by localized application of appropriate anti-thrombus or anti-clotting drugs in a biodegradable formulation, which act for a period of time sufficient to achieve this purpose. Some difficulty is encountered in providing a stent surface which is suitable for retention of the necessary drug(s).

At the outward facing surface of the stent in contact or engagement with the inner lining of the vessel, tissue irritation can exacerbate the same type of trauma that occurs during an angioplasty procedure, and possible restenosis. It is desirable to provide a timed release of anti-fibrotic drug(s) from the stent surface to avoid hyperplasia and recurrence of blockage at the stent site.

Another factor affecting the choice of the stent and the stent material is the possibility of allergic reaction of the patient to the stent implant. Biomaterial coatings can be helpful, but a statistically significant percentage of patients are allergic to materials of which some stents are composed, including chrome, nickel, and medical grade 316L stainless steel, which contains about 20% nickel. For such patients, the allergic reaction may be sufficient that stent implant is contraindicated. Wholly biodegradable stents of possibly sufficient radial strength are currently undergoing tests and may prove suitable in such cases.

It is essential that the implanting surgeon be able to see the progress of the stent as it is being inserted into place at the desired target site in the body, and for purposes of examination from time to time thereafter at the implant site, typically by X-ray fluoroscopy. The wall of the stent must be sufficiently thick to withstand the vessel wall recoil after deployment at the target site, but to allow the stent to be seen on the fluoroscope. Various materials, such as 316L stainless steel, possess suitable mechanical strength. Typical stent wall or wire thicknesses have ranged from 70 to 200 microns (or micrometers, $\mu$m). A 70 to 80 $\mu$m 316L steel stent offers sufficient strength to resist recoil so as to maintain a lumen diameter close to the diameter achieved at full deployment by balloon inflation. This relatively thin and tiny metal structure creates little shadow on a fluoroscopic picture, however, since the X-ray absorption of the metal is low. Increasing the wall thickness of the stent to enhance its radiopacity makes the stent less flexible, which makes it more difficult to maneuver the stent through narrow vessels. Greater wall thickness also makes it necessary to apply a larger radial force by balloon inflation during deployment of the stent, with concomitant increased risk of balloon rupture.

It follows that a suitable stent should possess at least the features of flexibility, resistance to vessel recoil, successful interventional placement, good radiopacity, sufficient thinness to minimize obstruction in the vessel being held open, and avoidance of vessel re-occlusion. Stent design plays an important role in influencing these features, together with proper selection or fabrication of the material of which the stent is composed.

Aside from vascular usage, other ducts or tracts of the human body in which a stent might be installed to maintain an open lumen include the tracheo-bronchial system, the biliary hepatic system, the esophageal bowel system, and the urinary tract. Many of the same requirements are found in these other endoluminal usages of stents.

Despite improvements in the design and construction of coronary stents, restenosis remains a problem. One major contributing factor is the inability of the body to incorporate the implanted foreign material quickly. Basic research with cell cultures and animal experiments have demonstrated that the degree of endothelialization of the foreign body determines the amount of the restenosis. Although an assumption among industry practitioners and researchers has been that a highly polished and smooth surface is beneficial to prevent stent thrombosis and to facilitate endothelialization, experiments have indicated that this is not entirely true.

A significant reason for the lack of a high clinical success rate with electropolished stents is the fact that the smooth muscle cells which seek to envelop a foreign body, such as a stent strut into the vessel wall, require a higher degree of proliferation to cover the foreign body. The continuing flow of blood with a high pressure and high shearing stress prevents the migration of smooth muscle cells, which proliferate from the media and adventitial cells of a stented vessel such as a coronary artery. It has been shown that a slightly rough surface considerably facilitates the coverage by smooth muscle cells, leading to a functional endothelial layer even after 10 to 14 days after stent implantation. A single layer of endothelial cells has been found to seal the neointima and thereby prevent the stimulus which facilitates and enhances the proliferation of cells beyond mere coverage of the foreign body.

The thinner the stent strut, the less the lumen of the stented vessel is obstructed. Moreover, a thin stent is more easily covered by a neoendothelial build-up. Accordingly, it is desirable to make the stent wall as thin as can be practically achieved. But the fluoroscopic visibility of stainless steel in a thickness below 60 $\mu$m is very poor because of the limited extinction of x-rays by such a thin metal tube.

The '045 patent discloses a vascular or endoluminal stent, composed of medical grade implantable 316L stainless steel, for example, which is covered with a very thin, highly adherent layer of gold or other noble metal, such as platinum, or an alloy which is primarily gold or other noble metal, or other metal having a high Z-number. Since gold has a six times (6×) higher radiopacity than stainless steel, a 10 $\mu$m layer of gold provides fluoroscopic visualization equivalent to 60 $\mu$m thickness of stainless steel. Thus, a gold coating, for example, offers a radiopaque surface that renders the stent highly visible under fluoroscopy as it is being advanced through the vessel lumen to the desired site of deployment, as well as after deployment. Such a coating may be provided in a very thin layer, so that the stent wall thickness is determined almost solely by considerations of mechanical strength, with consequent reduction of stent external diameter over what would be required if enhanced radiopacity of the base metal were an overriding factor.

The noble metal layer may be ultra-thin and is applied to cover the entire stent—interior as well as exterior surfaces and all edges bounding the internal openings in the wall and the ends thereof if the stent is of the hollow, open-ended tube type, or the entire surface of the wire if the stent is of the wire type. The layer is applied in a way—including a two-layer application—to assure an absolute adherence to the underlying metal of the stent and thereby to prevent even any cracking or defects in the homogeneous nobler metal layer, much less resist peeling or flaking of the layer during insertion, and especially during expansion of the diameter of the stent as it is being deployed in final position in the artery at the target site.

As pointed out in the '045 patent, gold is non-irritating and substantially non-allergenic, which allows a gold-plated stent to be implanted even in patients with severe materials allergies. Additionally, the gold layer offers a surface of substantially non-thrombogenic characteristics, and therefore reduces the likelihood of an acute closure of the vessel in which it is implanted. And if an acute closure is avoided, it is much more likely that a chronic closure of the lumen will be avoided in the region of the vessel occupied by the stent. A gold-coated stent exhibits about 40% or less thrombus formation than that of uncoated metal stents, especially steel.

The disadvantage of reduced mechanical strength of noble metals such as gold or platinum—which makes them unsuitable if sought to be used alone for application in the human vascular system—is overcome by the use of a core composed of a material such as stainless steel, having considerably better mechanical properties than the noble metal. And the presence of an uninterrupted (i.e., without cracks or related defects), substantially uniform, homogeneous coating of gold or other noble metal has been found to be of great importance to avoid a galvanic potential which could ultimately lead to corrosion of the underlying steel or lesser metal. Such a corrosive environment is unacceptable in a stent to be permanently implanted in the body. The highly adherent noble metal coating provides long-term stability and excellent clinical results, and its relatively softer constituency compared to the underlying rigid core of the stent allows at least a slight configurational change upon expansion of the stent to its fully deployed state.

The '045 patent describes a preferred application of an initial layer of gold by vaporization in a vacuum chamber and then accelerating the gold ions onto and in adherent relationship with the surface of the underlying metal, with stable anchoring thereto, to a thickness of 1 $\mu$m or more, followed by a galvanic process to provide a relatively uniform, overall layer thickness of from about 3 to about 6 $\mu$m including the initial foundation layer. This achieves a highly adherent, tight coverage, and firm, yet lineally extensible, bond between the base metal of the stent core or carrier and the noble metal of the outer layer.

The co-pending '053 application describes, in a preferred embodiment, a stent whose sidewall includes a first solid layer or thickness of a biocompatible base metal, and a second porous layer or thickness which is composed of spherically-shaped metal particles, composed at least in part of a noble metal, which are bonded together to leave spaces between the particles which may serve as a repository for drugs to assist in maintaining the lumen of the vessel open. The second thickness overlies the first thickness in tightly adherent relation thereto, and has a radiopacity which substantially exceeds that of the first thickness.

An embodiment of a stent described in the '053 application includes at least one drug selected from a group consisting of anti-thrombotic, anti-platelet, anti-inflammatory and anti-proliferative drugs, residing in the repository. A biodegradable carrier retains the drugs for timed release from the repository when the stent is deployed at the selected implant site in the blood vessel. Alternatively, the spacing of the metal particles may be such to provide a timed release of the drugs from the repository. Preferably, the particles are located with larger diameter sizes adjacent and bonded to the surface of the first thickness and with progressively smaller diameter sizes bonded together up to the outermost region of the second thickness. In either event, the anti-platelet and/or anti-thrombotic drugs are preferably infused into the porous layer repository, i.e., into the spaces or interstices between the particles, existing at the inward facing surface (and if desired, at directly adjacent edges of the openings) of the stent to inhibit clogging of the lumen as a result of interaction between the stent itself and the blood flow therethrough. The anti-inflammatory and/or anti-proliferative drugs are preferably infused into the repository existing at the outward facing surface (and if desired, at directly adjacent edges of the openings) of the stent to inhibit restenosis as a result of fibrosis or proliferation of tissue from trauma to the inner lining of the vessel arising from contact with the stent.

The '053 application also describes a third layer of a ceramic-like material—preferably of either iridium oxide or titanium nitrate—which is applied as a coating overlying exposed surfaces of the metal particles in tightly adherent relation to the second thickness at those surfaces, without filling or blocking the spaces between the particles, so that the repository for drugs originally formed in the second layer remains available. The desired drugs may be infused into spaces between particles, in preferential locations as noted above, for retention and dispensing in the same manner as if the third layer had not been applied. Additionally, the ceramic-like material is resistant to tissue irritation to further avoid traumatic response during contact of the stent with the inner lining of the vessel at the implant site.

The base metal may be 316L stainless steel, chromium, nickel, titanium, iridium, or nitinol, for example, nominally of 70 $\mu$m thickness. The metal particles of platinum-iridium alloy have diameters ranging from about 50 to 500 nanometers (nm), and the porous layer is applied atop the base metal to a thickness in a range from about 4 to 8 $\mu$m. The iridium oxide or titanium nitrate is coated on surfaces of the metal particles to a thickness in a range from approximately 50 to 500 nm. The desired drugs or other selected agents are infused into the reservoir provided by the voids or interstices between particles of the porous layer. Timed release of the drugs may be achieved by incorporating them in a biodegradable carrier.

The '561 patent also discloses use of a stent structure having three fundamental layers, a first underlying layer of a base metal that functions to provide high mechanical strength, a second intermediate layer that functions to provide high fluoroscopic visibility—preferably a noble metal layer or alloy thereof—, and a top layer of a particularly beneficial biocompatible material—preferably a ceramic-like material such as iridium oxide or titanium nitrate. The intermediate layer of elemental or alloy of a noble metal is uninterrupted, highly adherent for tight coverage and substantially uniform thickness. Such an intermediate layer tends to assure avoidance of a galvanic potential that would lead to corrosion of the lesser, base metal, including such a condition that may obtain with a layer of ceramic-like metal overlying the base metal at points where fissures might exist were it not for the uninterrupted presence of the intermediate noble metal layer. The three layer stent of the '561 patent exhibits mechanical strength, small physical dimensions, increased visibility, long-term stability, and a highly biocompatible surface that enables rapid endothelialization with low occurrence of restenosis.

Gene therapy or transfer is used as an alternative to drugs to inhibit proliferation of smooth muscle cells, to prevent restenosis that could block the lumen of the vessel in which the stent is deployed. In this technique, a viral vector transfers at least part of the genetic information of interest to the target cell. A gene transfer agent constituting the viral vector or virus is incorporated in a biodegradable carrier, or microspheres or liposomes as the viral vector are contained in solution, and the combination is infused into the reservoir of the multilayer stent from which it is released in a substantially programmed manner.

SUMMARY OF THE INVENTION

The present invention provides a stent having a tubular metal base adapted to be expanded from a first vessel-navigable diameter to a larger second vessel-deployed diameter. A thin, continuous intermediate layer of noble metal or alloy thereof selected from a group consisting of niobium, zirconium, titanium and tantalum, is applied or deposited to overlie and tightly adhere to an exposed surface area of the tubular metal base. Then, a biocompatible outer layer of iridium oxide is applied to overlie and adhere to the intermediate layer. The outer layer has a relatively rough surface with interstices into which beneficial drugs or other substances or agents may be infused, with or without a biodegradable carrier, to preclude occlusion from restenosis or thrombosis during the acute stage following deployment of the stent.

BRIEF DESCRIPTION OF THE DRAWINGS

The above and still further aims, objectives, features, aspects and attendant advantages of the present invention will become apparent to those skilled in the art from the following detailed description of a best mode presently contemplated of practicing the invention by reference to certain preferred embodiments and methods of manufacture thereof, taken in conjunction with the accompanying drawings, in which.

DESCRIPTION OF BEST MODE IN PREFERRED EMBODIMENTS

Certain portions of the aforementioned related patents and application are repeated in some detail herein, for the sake of convenience to the reader.

Figure 1A:
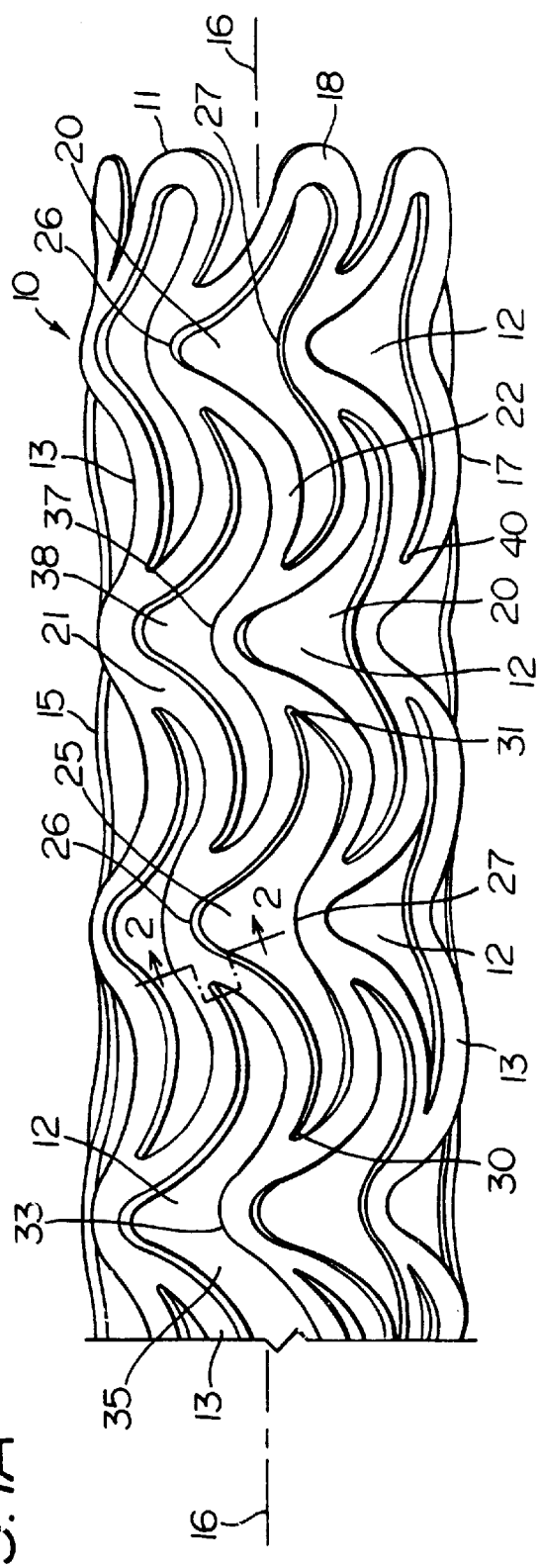
FIGS. 1A and 1B are a fragmentary side view and enlarged detail of an embodiment of a stent with an intermediate layer overlying its wall according to the present invention.

In FIG. 1A (not to scale) stent 10 is illustrated as being fabricated as a hollow tubular self-supporting structure or member 11 composed of a biocompatible metal such as medical grade 316L stainless steel, although other metals may alternatively be used, such as titanium, iridium, or nitinol, for example. The tubular member is provided with a multiplicity of through-holes or openings 12 through sidewall 15, defined and bounded by a plurality of struts or links 13, which enables expansion of the stent diameter when the device is to be deployed at a target site in a vessel, duct or tract of the human body. The openings 12 may be precisely cut out to form a latticework sidewall using a narrow laser beam of a conventional laser following a programmable pattern. The removed material that formerly occupied openings 12 is discarded following the cutting.

By way of example and not of limitation, the resulting pattern in the latticework sidewall 15 is a network of interconnected struts 13 which are optimized for orientation predominantly parallel to the longitudinal axis 16 of the tube 11, with none of the struts oriented perpendicular (i.e., transverse) to the axis 16, so that no strut interconnecting any other struts in the latticework is oriented to lie completely in a plane transverse to the longitudinal axis, without running from one end of the stent to the opposite end. This type of structure, which is described in detail in applicant's co-pending application Ser. No. 08/933,627, provides a relatively very low friction characteristic (or coefficient of friction) of the outer surface 17 of the stent, to ease advancement of stent 10 in a vessel, duct or tract to a site for deployment. The network or latticework of struts 13 may define a series of longitudinally repeating circumferential rows 20 of openings 12, in which each opening has a shape which resembles the outline of a handlebar moustache, or of a Dutch winged cap, with each opening bounded by alternating links in wavelets of higher and lower crests in successive rows of each circumferential column displaced along the length of the cylindrical element. If viewed upside down, the openings have a shape resembling the outline of a ram's head with horns projecting at either side upwardly from the head and then downwardly, each opening bounded by alternating links in wavelets of shallower and deeper troughs in successive rows of each circumferential column displaced along the length of the cylindrical element.

Each pair of struts such as 21, 22 bounding an opening 12 in any given row 25 are in the shape of circumferentially displaced wavelets with adjacent circumferentially aligned higher and lower crests 26, 27, respectively, in which the wavelets intersect (30) one another at one or both sides of the crests (30, 31). The intersection 30 of struts (or wavelets) at one side of the adjacent circumferentially aligned crests 26, 27 of row 25 is tangential to a crest 33 of the immediately adjacent row 35, and the intersection 31 of struts (or wavelets) at the other side of those crests is tangential to a crest 37 of the immediately adjacent row 38. Interconnecting points such as 40 between the struts may be notched to enhance symmetrical radial expansion of the stent during deployment thereof.

When the stent 10 is crimped onto a small diameter (low profile) delivery balloon (not shown), the adjacent circumferentially aligned crests of each row move closer together, and these portions will then fit into each other, as the pattern formed by the latticework of struts allows substantial nesting together of the crests and bows, which assures a relatively small circumference of the stent in the crimped condition. Such a stent is highly flexible, and is capable of undergoing bending to a small radius corresponding to radii of particularly tortuous coronary arteries encountered in some individuals, without permanent plastic deformation.

As the stent 10 is partially opened by inflation of the balloon during deployment, the adjacent crests begin to separate and the angle of division between struts begins to open. When the stent is fully expanded to its deployed diameter, the latticework of struts takes on a shape in which adjacent crests undergo wide separation, and portions of the struts take on a transverse, almost fully lateral orientation relative to the longitudinal axis of the stent. Such lateral orientation of a plurality of the struts enables each fully opened cell to contribute to the firm mechanical support offered by the stent in its fully deployed condition, to assure a rigid structure which is highly resistant to recoil of the vessel wall following stent deployment. The particular configuration of the stent structure, while highly desirable, is illustrative only and not essential to the principles of the present invention.

The stent may be pre-opened after fabrication to relieve stresses. Pre-opening produces a stent inner diameter that allows the stent to slide comfortably over the uninflated mounting balloon, for ease of crimping the stent onto the balloon. Annealing may be performed after pre-opening by heating the stent structure to an appropriate temperature for a predetermined interval of time.

Figure 1B:
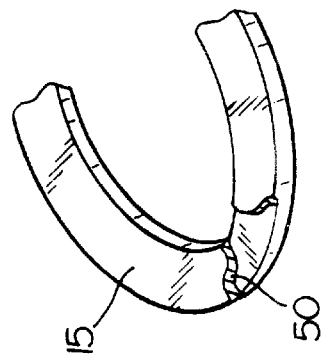

Before or after the pre-opening and annealing steps, the stent is coated with a thin, tightly adherent intermediate layer 50 (FIG. 1B, shown partly disrupted for clarity) of noble metal or an alloy thereof, preferably selected from a group consisting of niobium, zirconium, titanium and tantalum. This intermediate layer is applied to cover the entire exposed surface of the tubular metal base wall 15 of the stent. Preferably, layer 50 has a thickness in the range from approximately 1 $\mu$m to approximately 20 $\mu$m, and more preferably about five $\mu$m.

In a preferred embodiment of the stent, intermediate layer 50 is composed of an alloy of niobium and zirconium, the amount of zirconium being tantamount to a trace ranging from about one percent to about three percent by weight of the total, for hardness. The alloy may be deposited in a thin layer on the metal base by any conventional process, to produce a firm, tightly bonded, extremely thin foundation layer, which allows the intermediate layer to flex without suffering fracture, cracking, peeling or flaking at times when the stent is undergoing mechanical stress and distortion, such as during the pre-opening, crimping, and expansion-during-deployment of the stent.

Alternatively, the intermediate layer 50 may be composed of an alloy of titanium and tantalum, with the amount of tantalum in the alloy being in a range from about 30% to about 40% by weight. In either event, the coated stent is preferably subjected to a cleansing step by heating under vacuum to a temperature which will depend upon the nature of the coating and the underlying material.

Figure 2:
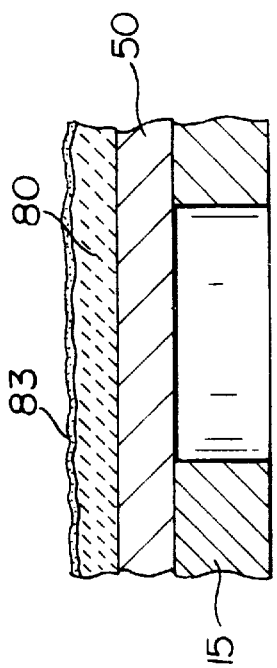
FIG. 2 is a cross-sectional view of the stent illustrating intermediate and outer layers.

A stent 10 fabricated according to the present invention is composed of three different primary or fundamental layers as shown in the greatly exaggerated fragmentary cross-sectional view of FIG. 2, taken through the line 2—2 of FIG. 1A. By "primary" and "fundamental", as used here, it is meant and intended that although the stent may have additional layers, coatings or films, the three layers—including the metal base sidewall 15 and intermediate layer 50 which have been described thus far—are essential to the favorable characteristics of the stent.

The third or outer layer 80 is preferably composed of a ceramic-like metal material such as oxide, hydroxide or nitrate of metal, preferably iridium oxide (IROX) or titanium nitrate, as a biocompatible layer that serves a primary purpose of avoiding tissue irritation and thrombus formation. Outer layer 80 may be deposited as an inert coating over the surface(s) of the underlying intermediate layer 50 by any known method, preferably to a thickness in the range from about 500 nm to about 1,500 nm (=1.5 $\mu$m). Like the intermediate layer, outer layer 80 is preferably applied to both sides (and indeed, all exposed surfaces) of the wall 15 of stent 10, so that it is the surface that contacts both the inner lining of the vessel and the blood flowing through the lumen of the vessel in which the stent is implanted (deployed).

A high voltage sputtering process is among many suitable processes that may be used to form this outermost coating. Others include anionic oxidation and thermal oxidation. Oxalic acid, application of current and heat, and additional use of an ultrasound bath have been found to produce a very tight adhesion of iridium oxide to the underlying intermediate layer. Suitable processes for forming iridium oxide or titanium nitrate layers also have been developed and can be performed by Hittman Materials & Medical Components, Inc. of Columbia, Md., for example. Preferably, the outer layer 80 is be formed with a comparatively or relatively rough porous surface, so that interstices thereof form reservoirs or repositories therein for infusion and retention of beneficial drugs or other substances. For the sake of clarity, outer layer 80 is shown without the extremes of interstices that are actually present.

The intermediate noble metal or alloy layer 50 precludes the occurrence of a galvanic potential that might cause corrosion of the base layer. It also serves to enable flexing of the stent over a vast number of cycles encountered in actual use without loss of the overlying iridium oxide or titanium nitrate coating from flaking, shedding or disintegration. Desired anti-inflammatory and/or anti-proliferation drugs may be applied to enter the interstices of the rough outward facing surface and adjacent edges of openings of the stent. The interstices may be at least partially filled with a substance selected to enhance the compatibility of the stent in a vessel, duct or tract of the body in which the stent is to be implanted. For example, the desired anti-thrombotic and/or anti-platelet agents are applied to enter the interstices at the rough inward facing surface and adjacent edges of openings of the stent. By virtue of this repository, the drugs or other substances or agents are, to an extent, time released therefrom to provide a primarily acute response to tissue trauma and clotting mechanisms.

Additionally, or alternatively, timed release of the beneficial drugs from the interstices of the outermost layer 80 may be controlled by incorporating the drugs in a biodegradable carrier 83 (FIG. 2). In that case, time-controlled release of the drugs takes palce with degradation or disintegration of the carrier itself, so that the drug or other agent remains captive within the carrier until it is dispensed or released, i.e., freed from its host, by progressive dissolution upon continuing diffusion of the carrier from the reservoir. The drug tends to act locally rather than systemically in such an arrangement.

As an alternative to the infusion or incorporation of anti-proliferative or anti-inflammatory drugs into the reservoir along the outward facing porous structure of the outer layer, gene therapy may be used to inhibit the smooth muscle cell growth that leads to neointima and restenosis. Interstices of the rough porous surface of the outer layer at both interior and exterior surfaces of said stent may be at least partially filled with substances that genetically interfere with cells at the target lesion site in the vessel at which the stent is to be implanted.

In principle, a viral vector may be used to transfer the desired information into the genome of the target cells. Viruses capable of such gene transfer are, for example, adenovirus and herpervirus, or fractions of the virus. By viral transfer, which is believed to occur by virtue of absorption and diffusion, part of the genetic information of interest is provided to the target cell. Such information can relate to several mechanisms of smooth muscle cell proliferation, with the aim of inhibiting restenosis which, if unchecked, could result in at least partial and perhaps complete blockage of the vessel's lumen, despite the presence of the deployed stent at the site.

One important technique involves blocking the proliferation stimulating factors such as cytoKines, n Fkappa b, platelet derived growth factors or other growth factors that originate from platelet deposition, thrombus formation, mechanical stress, or injury and inflammation. The applicant herein is currently investigating whether selective inducement of apotosis—or programmed cell death—may be achieved via the fas-ligand, which would enable a programmed intervention against overshooting cellular proliferation in a narrowly controlled region of the tissue.

The virus transfer is performed by incorporating the gene therapy agent—a viral vector or virus of the above-mentioned type that contains the viral genetic information desired to be transferred to the target cell(s)—into a biodegradable carrier for release from the reservoir into which it has been infused and dispensed by the process of biodegradation. Alternatively, the release to effect the gene therapy may be accomplished by release from a solution in the reservoir which contains liposomes as the viral vector.

The three layer structure can be produced with a composite thickness of less than 60 $\mu$m. The stainless steel core or base metal wall 15 may be fabricated in a thickness of approximately 35 $\mu$m, which offers sufficient mechanical strength to resist the natural recoil of the blood vessel wall following deployment of the stent. The noble metal or alloy intermediate layer 50 is applied in a preferably 5 $\mu$m thickness to all exposed surfaces of the base layer, giving a total additional thickness of 10 $\mu$m to the structure, and serving to avoid a galvanic potential. The outermost IROX layer or oxide, hydroxide or nitrate of noble metal is applied to a thickness of up to about 1.5 $\mu$m atop the intermediate layer as a biocompatible surface for the overall stent.

Although a best mode of practicing the invention has been disclosed by reference to certain preferred embodiments and methods, it will be apparent to those skilled in the art from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A stent, comprising a tubular metal base adapted to be expanded from a first vessel-navigable diameter to a larger second vessel-deployed diameter; a thin, continuous intermediate layer of noble metal or alloy thereof selected from a group consisting of niobium, zirconium, titanium and tantalum, overlying and tightly adherent to an exposed surface area of said tubular metal base; and a biocompatible outer layer of iridium oxide overlying and adherent to said intermediate layer.

2. The stent of claim 1, wherein the composite thickness of the wall of said tubular metal base, and said intermediate and outer layers thereon is less than approximately 60 $\mu$m.

3. The stent of claim 1, wherein said intermediate layer is an alloy composed of niobium and zirconium.

4. The stent of claim 3, wherein the amount of zirconium in said intermediate layer alloy is in a range from about 1% to about 3% by weight of the total intermediate layer.

5. The stent of claim 1, wherein said intermediate layer is an alloy composed of titanium and tantalum.

6. The stent of claim 5, wherein the amount of tantalum in said intermediate layer alloy is in a range from about 30% to about 40% by weight.

7. The stent of claim 1, wherein said outer layer has a rough surface with interstices thereof at least partially filled with a substance selected to enhance the compatibility of the stent in a body in which said stent is to be implanted.

8. The stent of claim 1, wherein said outer layer has a rough surface with interstices thereof at both interior and exterior surfaces of said stent at least partially filled with drugs selected to inhibit closure of a central lumen at a site in the body at which said stent is to be implanted.

9. The stent of claim 8, wherein said drugs are contained within a biodegradable carrier for release of said drugs during disintegration of the carrier.

10. The stent of claim 1, wherein said outer layer has a rough surface with interstices thereof at both interior and exterior surfaces of said stent at least partially filled with substances that genetically interfere with cells at a site in the body at which said stent is to be implanted.

* * * * *